(12) United States Patent
Maxeiner et al.

(10) Patent No.: US 8,291,903 B2
(45) Date of Patent: Oct. 23, 2012

(54) WATER TRAP WITH AN EMPTYING DEVICE

(75) Inventors: Thomas Maxeiner, Lübeck (DE); Gerd Peter, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1097 days.

(21) Appl. No.: 12/185,974

(22) Filed: Aug. 5, 2008

(65) Prior Publication Data

US 2009/0084383 A1 Apr. 2, 2009

(30) Foreign Application Priority Data

Sep. 28, 2007 (DE) .......................... 10 2007 046 533

(51) Int. Cl.
*A62B 7/10* (2006.01)
*B01D 53/26* (2006.01)
(52) U.S. Cl. .............................. 128/205.12; 128/205.27
(58) Field of Classification Search ............. 128/205.12, 128/205.27
See application file for complete search history.

(56) References Cited

U.S. PATENT DOCUMENTS

| | | | | |
|---|---|---|---|---|
| 5,209,761 A | * | 5/1993 | Ivester et al. ................... 95/271 |
| 5,368,021 A | * | 11/1994 | Beard et al. .............. 128/205.12 |
| 6,117,214 A | | 9/2000 | Peter et al. |
| 6,184,818 B1 | * | 2/2001 | Meinel ........................... 342/124 |
| 6,220,242 B1 | * | 4/2001 | Wallin ...................... 128/203.12 |
| 6,606,994 B1 | * | 8/2003 | Clark ........................ 128/205.12 |
| 2006/0005312 A1 | * | 1/2006 | Reddy et al. ....................... 4/668 |
| 2006/0186031 A1 | * | 8/2006 | Fick et al. ...................... 210/235 |
| 2006/0243345 A1 | * | 11/2006 | Lease ............................... 141/95 |

FOREIGN PATENT DOCUMENTS

DE 199 01 590 C1 7/2000

OTHER PUBLICATIONS

Monsi, Radio Frequency—Wireless Level Detection System by Using Spacial Field Attenuation (DOI 10.1109/SENSORCOMM. 2007.49).*

* cited by examiner

*Primary Examiner* — Lynne Anderson
*Assistant Examiner* — Peter S Vasat
(74) *Attorney, Agent, or Firm* — McGlew and Tuttle, P.C.

(57) ABSTRACT

A breathing gas system and water trap (1) is improved in respect to the reliability of operation and has an emptying device. The water trap (1) has a gas inlet (4), which meets a first water separating membrane (5) via a connection line. The connection line leads into a water tank (20) located deeper in the incoming flow direction from the first water separating membrane (5) and into a gas measuring device (2) with vacuum on the discharge side from the first water separating membrane (5) from the water trap (1). The water tank (20) has a rinsing gas flow line, which is arranged above the liquid level, leads upward via a gas-permeable membrane (6) and is likewise connected to the applied vacuum of the gas measuring device (2). The water tank (20) has a water transport line for emptying the water tank (20), which water transport line extends into the liquid and is provided with a downstream vacuum via a nonreturn valve (7) and a downstream liquid pump (17) or via a solenoid valve (21). The water trap (1) is equipped with a filling level detection system (8, 9, 22; 8, 9, 13; 8, 10), which is connected to a control and analyzing unit (3). The control and analyzing unit (3) is connected to the liquid pump (17) or to the solenoid valve (21), so that the water tank (20) can be emptied as a function of the signal of the filling level detection system (8, 9, 22; 8, 9, 13; 8, 10).

17 Claims, 1 Drawing Sheet

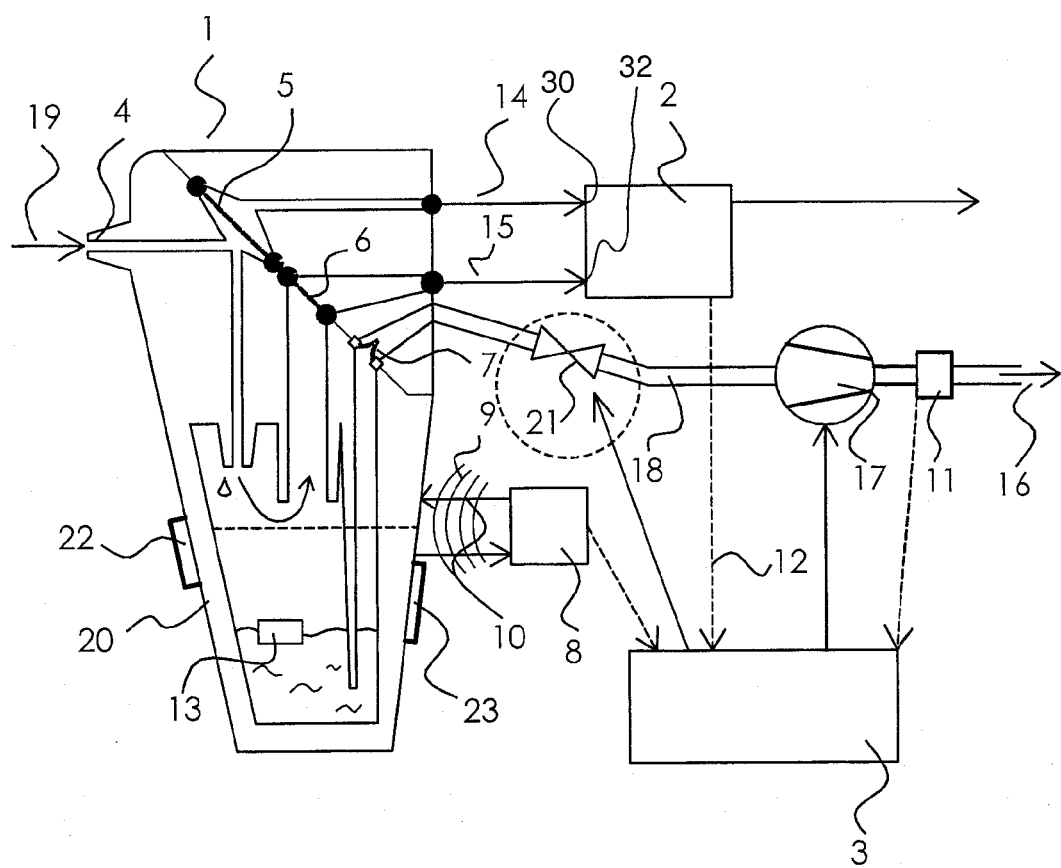

="" # WATER TRAP WITH AN EMPTYING DEVICE

CROSS REFERENCE TO RELATED APPLICATIONS

This application claims the benefit of priority under 35 U.S.C. §119 of German Patent Application DE 10 2007 046 533.7 filed Sep. 28, 2007, the entire contents of which are incorporated herein by reference.

FIELD OF THE INVENTION

The present invention pertains to a water trap with an emptying device.

BACKGROUND OF THE INVENTION

A prior-art water trap for use in a breathing gas line of an anesthesia apparatus or respirator for separating moisture contained in the breathing gas appears, for example, from DE 199 01 590 C1 (corresponding to U.S. Pat. No. 6,117,214). The breathing gas, from which the moisture has been removed, flows downstream of the water trap especially into an infrared optical measuring unit for the analysis or determination of the concentration of constituents of the breathing gas or gaseous anesthetics contained in the breathing gas. Just like the water trap according to the present invention, the prior-art water trap can be replaceably connected to a holder of an anesthesia apparatus.

The water traps used so far as described in the area of medical engineering include both water traps for single-time use and water traps for multiple use, the water container for the moisture collected being emptied in the latter case, in general, by the operating staff after a certain operating time by means of a syringe and put out of operation after certain intervals of use. It may happen that the gas measurement will fail if the replacement intervals are not observed.

SUMMARY OF THE INVENTION

The object of the present invention is to provide a water trap improved in terms of reliability of operation and operation.

According to the invention, a water trap is provided that is connected to a gas measuring device. The water trap comprises a gas inlet, a connection line, a first water separation membrane, a water tank and a gas-permeable membrane. The gas inlet leads to the first water separation membrane via the connection line. The connection line leads from the first water separation membrane into the water tank on an incoming flow side of the water separation membrane, and leads to the gas measuring device on an outflow side of the water separation membrane and with a vacuum of the gas measuring device applied thereto. The water tank has a rinsing gas flow line arranged above a liquid level and leads upward via the gas-permeable membrane to the gas measuring device and with the vacuum of the gas measuring device applied thereto. A water transport line is associated with the water tank and extends below the liquid level of the water tank for the emptying the water tank. Either a nonreturn valve with a downstream liquid pump for providing a downstream suction in the water transport line or a solenoid valve with downstream vacuum in the water transport line is provided. A filling level detection system is connected to a control and analyzing unit that is connected to the liquid pump or to the solenoid valve so that the water tank can be emptied as a function of a signal of the filling level detection system.

The filling level detection system may have a detector unit. The filling level detection system may have at least one of a RFID tag arranged on the outer side of the water tank and a transponder designed as a float element for detecting the changed liquid level in the water tank by means of the detector unit based on a variable received signal or the field attenuation through the liquid.

The filling level detection system may comprise an optical transmitting and receiving means.

The solenoid valve may be connected to a bronchial suction of an anesthesia apparatus to provide the downstream vacuum.

A flow sensor may be connected to the control and analyzing unit. Such a flow sensor may be arranged in the water transport line for detecting the amount of liquid being delivered.

The gas measuring means may be connected to the control and analyzing means by a signal transmission provided from the gas measuring means to the control and analyzing means so that one of the liquid pump and the solenoid valve are controlled as a function of pressure and/or volume flow signals detected in the gas measuring means at an outlet of the connection line and the rinsing gas flow line.

The water separating membrane and the gas-permeable membrane may be formed of a hydrophobic gas-permeable material. The hydrophobic gas-permeable material may be one of Polytetrafluoroethylene (PTFE) or a PTFE copolymer.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a schematic view showing exemplary embodiments of a water trap with the essential components according to the present invention.

DESCRIPTION OF THE PREFERRED EMBODIMENTS

Referring to the drawings in particular, the breathing gas 19 to be analyzed flows due to a vacuum applied, for example, as expired breathing gas of a patient connected to an anesthesia apparatus via the water trap 1 into a gas measuring means 2 for determining the concentrations of constituents of the gas. Such a gas measuring means may be, for example, an infrared optical, electrochemical and/or paramagnetic measuring means. The breathing gas 19 first enters the water trap 1 at the gas inlet 4. The gas to be measured enters the gas measuring means 2 in the measured gas flow 14 via a measuring gas input 30 which draws a vacuum.

The water entrained in the gas flow is separated at the water separation membrane 5 made of a hydrophobic membrane material, such as Polytetrafluoroethylene (PTFE —also known as Teflon®), and delivered into the water tank 20 by means of a vacuum-operated rinsing gas flow 15 connected to a rinsing gas input 32 and supported by the force of gravity. The second, likewise water-impermeable, but gas-permeable membrane 6 made of a hydrophobic material prevents water from accidentally entering the connected pneumatic system of the gas measuring means 2 via the rinsing gas flow branch. The separated water collects in the water tank 20 of the water trap 1.

The water level of the amount of water separated rises in the water tank 20 in the further course of the operation until the water tank is filled, so that emptying of the water tank 20 is necessary in order to make it possible to continue the gas measurement. According to the current state of the art, a water tank such as the water tank 20 is emptied by the operating staff manually, which is prompted either by a failure of the gas measurement, a visual checking of the water level in the preferably transparent water tank 20 or a warning signal of a filling level detection system.

According to the invention, a filling level detection system is provided based, for example, on:

a) the evaluation of pneumatic parameters in the measured gas and rinsing gas flow branch of the gas measuring means 2, with a signal transmission 12 to the control and analyzing unit 3; or b) an optical detection 10 of the water level by means of the detector unit 8, optionally by means of a float element 13; or c) on a filling level detector via the field attenuation of a detector unit 8 for an RFID tag 22 arranged on a diametrically opposite side of the water tank 20 from detector unit 8, as shown in the drawing, where the detector unit 8 is designed as a transmitting/receiving means.

The water tank 20 is preferably transparent to the wavelength of light used for the measurement for the optical detection of the filling level.

The mode of operation of the present automatic emptying device is as follows:

When the filling level detection system 10, 8 (infrared optical) or 9, 8 (electromagnetic/inductive) responds, a signal is sent to the control and analyzing unit 3. The control and analyzing unit 3 thereupon causes a liquid pump 17 to be switched on. The water is pumped by the liquid pump 17 via the nonreturn valve 7 and the flexible tube 18 to the liquid discharge line 16. Complete emptying of the water tank 20 is ensured, for example, by the on time of the liquid pump 17, the liquid pump 17 being actuated by the control and analyzing unit 3.

In a special embodiment, the amount of liquid pumped off is determined by flow measurement by means of the flow sensor 11, and the result is sent to the control and analyzing unit 3. Besides the duration of use, an intensity of use can thus also be recorded and updated by means of an additional RFID tag 23 as a criterion of wear and use for each water trap 1.

In an alternative embodiment, vacuum is generated for drawing off the contents of the water tank 20 by the bronchial suction present in anesthesia apparatuses, which is connected via the solenoid valve 21. The nonreturn valve 7 and the liquid pump 17 are not necessary in this case. The number of valve switchings of the solenoid valve 21 corresponds in this case to the number of emptying operations and can be used as a parameter of wear corresponding to the intensity of use.

The reading and/or data recording of the additional RFID tag 23 is carried out either by means of another contactless transmitting/receiving means, not shown, of the anesthesia apparatus, or it can be carried out, as an alternative, especially by means of the detector unit 8 already present for the RFID tag 22.

While specific embodiments of the invention have been shown and described in detail to illustrate the application of the principles of the invention, it will be understood that the invention may be embodied otherwise without departing from such principles.

What is claimed is:

1. A water trap for use with a breathing apparatus and connected to a gas measuring device, the water trap comprising:
   a gas inlet;
   a connection line;
   a first water separation membrane, said gas inlet leading to said first water separation membrane via said connection line;
   a water tank, said connection line leading from said first water separation membrane into said water tank on an incoming flow side of said water separation membrane, and leading to the gas measuring device on an outflow side of said water separation membrane and with a vacuum of the gas measuring device applied thereto;
   a gas-permeable membrane, said water tank having a rinsing gas flow line arranged above a liquid level and leading upward via said gas-permeable membrane to the gas measuring device and with the vacuum of the gas measuring device applied thereto;
   a water transport line associated with said water tank and extending below the liquid level of said water tank for the emptying said water tank;
   one of a nonreturn valve with downstream liquid pump for providing a downstream suction in said water transport line and a solenoid valve with downstream vacuum in said water transport line;
   a control and analyzing unit; and
   a filling level detection system connected to said control and analyzing unit, said control and analyzing unit being connected to said liquid pump or to said solenoid valve so that said water tank can be emptied as a function of a signal of said filling level detection system, said filling level detection system including an RFID tag and a detector unit arranged on diametrically opposite sides of said water tank, said detector unit transmitting a signal through said water tank to said RFID tag, and receiving a signal from said RFID tag through said water tank, said filling level detection system detecting a change in a liquid level in said water tank based on the received signal.

2. A water trap in accordance with claim 1, wherein:
   said filling level detection system detects the change in liquid level in said water tank based on field attenuation through the liquid.

3. A water trap in accordance with claim 1, wherein said filling level detection system comprises an optical transmitting and receiving means.

4. A water trap in accordance with claim 1, wherein said solenoid valve is connected to a bronchial suction of an anesthesia apparatus to provide said downstream vacuum.

5. A water trap in accordance with claim 1, further comprising a flow sensor connected to said control and analyzing unit, said flow sensor being arranged in the water transport line for detecting an amount of liquid being delivered.

6. A water trap in accordance with claim 1, wherein said gas measuring means is connected to said control and analyzing unit by a signal transmission provided from the gas measuring device to said control and analyzing unit so that said one of said liquid pump and said solenoid valve are controlled as a function of pressure and/or volume flow signals detected in the gas measuring device at an outlet of the connection line and the rinsing gas flow line.

7. A water trap in accordance with claim 1, wherein said first water separation membrane and said gas-permeable membrane are formed of a hydrophobic gas-permeable material.

8. A water trap in accordance with claim 7, wherein said hydrophobic gas-permeable material is one of Polytetrafluoroethylene (PTFE) or a PTFE copolymer.

9. A breathing gas apparatus using a water trap, the apparatus comprising:
  a medical device breathing gas line;
  a gas measuring device determining concentrations of constituents of gas from said medical device breathing gas line, said gas measuring device having a measuring gas input and a rinsing gas input;
  a water trap connected to the medical device breathing gas line upstream of the gas measuring device, the water trap comprising a gas inlet receiving breathing gas from the medical device breathing gas line, a connection line, a first water separation membrane, said gas inlet leading to said first water separation membrane via said connection line, a water tank, said connection line leading from said first water separation membrane into said water tank on an incoming flow side of said water separation membrane, and leading to said gas measuring device on an outflow side of said water separation membrane and with a vacuum of the gas measuring device applied thereto, a gas-permeable membrane, said water tank having a rinsing gas flow line arranged above a liquid level and leading upward via said gas-permeable membrane to said gas measuring device and with the vacuum of the gas measuring device applied thereto, a water transport line associated with said water tank and extending below the liquid level of said water tank for emptying said water tank, one of a nonreturn valve with downstream liquid pump for providing a downstream suction in said water transport line and a solenoid valve with downstream vacuum in said water transport line, a control and analyzing unit, and a filling level detection system connected to said control and analyzing unit, said control and analyzing unit being connected to said liquid pump or to said solenoid valve so that said water tank can be emptied as a function of a signal of said filling level detection system, said filling level detection system having a detector unit, said filling level detection system having a RFID tag arranged on an outer side of said water tank for detecting a change in liquid level in said water tank by means of said detector unit based on a variable received signal or field attenuation through the liquid.

10. A breathing gas system in accordance with claim 9, wherein said solenoid valve is connected to a bronchial suction of an anesthesia apparatus to provide said downstream vacuum.

11. A breathing gas system in accordance with claim 9, further comprising a flow sensor connected to said control and analyzing unit, said flow sensor being arranged in the water transport line for detecting an amount of liquid being delivered.

12. A breathing gas system in accordance with claim 9, wherein said gas measuring device is connected to said control and analyzing unit by a signal transmission provided from said gas measuring unit to said control and analyzing unit so that said one of said liquid pump and said solenoid valve are controlled as a function of pressure and/or volume flow signals detected in said gas measuring device at an outlet of the connection line and the rinsing gas flow line.

13. A breathing gas apparatus using a water trap, the apparatus comprising:
  a medical device breathing gas line;
  a gas measuring device connected to said medical device breathing gas line and determining concentrations of constituents of gas from said medical device breathing gas line, said gas measuring device having a measuring gas input and a rinsing gas input which both draw a vacuum;
  a water trap connected to, and positioned between, the medical device breathing gas line and said gas measuring device, said water trap comprising,
    a first water separation membrane having an incoming flow side and an outflow side,
    a gas inlet receiving breathing gas from said medical device breathing gas line and leading the breathing gas to said incoming flow side of said first water separation membrane,
    a liquid tank,
    a first connection line leading from said incoming flow side of said water separation membrane into said liquid tank,
    a second connection line leading from said outflow side of said water separation membrane to said measuring gas input of said gas measuring device,
    a second water separation membrane with first and second sides,
    a first rinsing gas flow line communicating between said liquid tank and said first side of said second water separation membrane,
    a second rinsing gas flow line communicating between said second side of said second water separation membrane and said rinsing gas input of said gas measuring device;
  a liquid transport line connected to said liquid tank for emptying said liquid tank;
  one of a nonreturn valve with downstream liquid pump for providing a downstream suction in said water transport line and a solenoid valve with downstream vacuum in said liquid transport line;
  a filling level detection system connected to said liquid tank for detecting a liquid level in said liquid tank, said filling level detection system including an RFID tag and a detector unit arranged on diametrically opposite sides of said liquid tank, said detector unit transmitting a signal through said liquid tank to said RFID tag, and receiving a signal from said RFID tag through said liquid tank, said filling level detection system detecting a change in a liquid level in said liquid tank based on the received signal;
  a control and analyzing unit connected to said filling level detection system and said one of said liquid pump and said solenoid valve so that said liquid tank can be emptied as a function of a signal of said filling level detection system.

14. A breathing gas system in accordance with claim 13, wherein:
  said one of said nonreturn valve with liquid pump and said solenoid valve is said solenoid valve;
  an anesthesia apparatus is provided with a bronchial suction, said solenoid valve is connected to said bronchial suction to provide a downstream vacuum and to empty said liquid tank.

15. A breathing gas system in accordance with claim 13, wherein:
  said control and analyzing unit includes a flow sensor for measuring an amount of liquid removed from said liquid tank, said control and analyzing unit recording the amount of liquid removed from the liquid tank.

16. A breathing gas system in accordance with claim 15, further comprising:

another RFID tag mounted on said liquid tank and storing information on a duration of use and an intensity of use of the liquid tank.

17. A breathing gas system in accordance with claim 13, wherein:
said detector unit sends signals to both said RFID tag and said another RFID tag, said detector unit sends signals to said another RFID tag to store the information on the duration of use and the intensity of use of the liquid tank, said detector unit sends signals to said RFID tag to detect the liquid level in said liquid tank.

* * * * *